(12) United States Patent
Haveri

(10) Patent No.: US 6,539,937 B1
(45) Date of Patent: Apr. 1, 2003

(54) METHOD OF MAXIMIZING THE MECHANICAL DISPLACEMENT OF A PIEZOELECTRIC NEBULIZER APPARATUS

(75) Inventor: Heikki Haveri, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 09/547,523

(22) Filed: Apr. 12, 2000

(51) Int. Cl.7 .............................................. A61M 11/00
(52) U.S. Cl. .............................. 128/200.21; 128/200.14
(58) Field of Search ....................... 128/200.14, 200.23, 128/200.16, 203.12, 203.16, 203.18, 200.21, 200.11, 200.24; 239/102.2, 102.1, 398, 690.1

(56) References Cited

U.S. PATENT DOCUMENTS

| | | | |
|---|---|---|---|
| 3,812,854 A | 5/1974 | Michaels et al. ............ 128/194 |
| 3,885,902 A | 5/1975 | Fujieda et al. ................. 431/1 |
| 4,044,297 A | 8/1977 | Nobue et al. .................... 323/4 |
| 4,901,034 A | 2/1990 | Frank-Peter .................... 331/4 |
| 5,217,165 A * | 6/1993 | Takahashi et al. ....... 239/102.2 |
| 5,312,281 A * | 5/1994 | Takahashi et al. ............. 446/25 |
| 5,443,059 A | 8/1995 | Koch et al. ............. 128/200.16 |
| 5,487,378 A * | 1/1996 | Robertson et al. ..... 128/200.14 |
| 5,511,726 A * | 4/1996 | Greenspan et al. ...... 239/102.2 |
| 5,518,179 A * | 5/1996 | Humberstone et al. .. 239/102.2 |
| 5,551,416 A * | 9/1996 | Stimpson et al. ...... 128/200.14 |
| 5,657,926 A * | 8/1997 | Toda ........................ 239/102.1 |
| 5,716,002 A * | 2/1998 | Haack et al. ............. 239/102.1 |
| 5,823,428 A | 10/1998 | Humberstone et al. ........ 239/4 |
| 5,881,716 A * | 3/1999 | Wirch et al. ............ 128/200.14 |
| 6,105,571 A * | 8/2000 | Coffee .................... 128/200.14 |
| 6,158,431 A * | 12/2000 | Poole ..................... 128/200.16 |
| 6,196,219 B1 * | 3/2001 | Hess et al. .............. 128/200.14 |
| 6,247,525 B1 * | 6/2001 | Smith et al. ........... 165/104.23 |
| 6,273,342 B1 * | 8/2001 | Terada et al. ............. 239/102.1 |
| 6,296,196 B1 * | 10/2001 | Denen et al. ............. 239/102.1 |
| 6,357,671 B1 * | 3/2002 | Cewers .................... 239/102.1 |

FOREIGN PATENT DOCUMENTS

WO    WO 01/76762    10/2001

* cited by examiner

Primary Examiner—Aaron J. Lewis
Assistant Examiner—Teena Mitchell
(74) Attorney, Agent, or Firm—Andrus, Sceales, Starke & Sawall, LLP

(57) ABSTRACT

A nebulizer apparatus to atomize liquid solutions or suspensions. The nebulizer is typically used in conjunction with a breathing circuit to deliver atomized medicine to a patient. A housing with an opening covered by a thin mesh plate is supplied with the liquid to be nebulized on an "on-demand" basis. The mesh plate or liquid is vibrated at ultrasonic frequencies to atomize the liquid as it passes through the plate into the breathing gases flowing through the breathing tube. The vibration is produced with a piezoelectric element. The most efficient point to produce vibrations is found by measuring current, voltage or phase angle taken by the piezoelectric element or by measuring the resistance of the strain gauge attached to vibrator.

20 Claims, 9 Drawing Sheets

METHOD OF MAXIMIZING THE MECHANICAL DISPLACEMENT OF A PIEZOELECTRIC NEBULIZER APPARATUS

BACKGROUND OF THE INVENTION

The present invention relates to an improved nebulizer apparatus. Nebulizers, or atomizers, are devices that generate a fine spray or aerosol, usually of liquid. A particularly useful application for nebulizers is to provide a fine spray containing a dissolved or a suspended particulate or colloidal pharmaceutical agent for administration to a subject by inhalation. Such inhalation treatment is highly effective for conditions affecting the subject's respiratory organs. Further, since the lungs are close to the heart and the blood circulatory system of the body, drug administration by inhalation provides an effective and rapid delivery system to all organs of the body.

In many cases, the nebulizer is placed directly in the mouth or nose of the subject so that the spray can be entrained in the respiratory gases inhaled during normal, spontaneous breathing of the subject. In other cases, the subject breathes with the aid of a respiratory ventilator. A typical ventilator has a breathing circuit comprising an inhalation limb and an exhalation limb connected to two arms of an Y-connector. The third arm of the Y-connector is connected, via a patient limb, to a mouthpiece, mask or endotracheal tube for the subject. The ventilator provides a complete or partial supply of respiratory gases to the subject through the inhalation limb during inhalation. The contraction of the subject's lungs discharges gas through the exhalation limb during exhalation. When a nebulizer is employed in conjunction with a ventilator, it is typically placed in the patient limb.

Nebulizers currently in use for ventilator applications generate the spray either pneumatically or by means of ultrasonic vibrations. Pneumatic nebulizers are typically used with a liquid, such as an aqueous drug solution. High pressure driving gas is conducted through a nozzle to draw the drug from a drug supply for the nebulizer. The drug is discharged against a baffle or other means in a gas space of the nebulizer, breaking the liquid into a fine spray. The gas space is in fluid communication with the inhaled gas pathway of the breathing circuit so that the gas flow expelled from the nozzle along with the nebulized drug is conducted to the breathing circuit and ultimately to the subject.

Disadvantages in the use of pneumatic nebulizers include the following. If the nebulizer adds a significant quantity of gas, for example, up to five liters/minute, into the breathing circuit, the breathing gas composition is affected. The driving gas is most often either oxygen or air and, particularly when a ventilator is used in the treatment of a child, the gas flow from the nebulizer may form a major portion of the inhalation gas flow. Because of the gas flow from the nebulizer, control over the inhalation gas composition is lost. Also, due to passage of the driving gas through the nozzle, impingement of the drug on the baffle, etc., pneumatic nebulizers are noisy. This may contribute to the discomfort of the subject. And, as controlling the commencing and stopping of a drug agent spray is difficult and is not very accurate, pneumatic nebulizers are commonly active during both inhalation and exhalation. This obviously decreases the efficiency of drug delivery as measured by ratio of the amount of drug supplied to the nebulizer and the amount of drug actually delivered into the subject's air ways.

In an ultrasonic nebulizer, the fine spray is produced by ultrasonic vibration of the liquid, as by a piezoelectric crystal. The liquid is dropped on, or otherwise applied to, the crystal. The on-off operation of such nebulizers is easier to control than for a pneumatic nebulizer. However, prior art ultrasonic devices require a large electrical power consumption to power the crystal and may not be able to nebulize colloidal or particulate suspensions. Partly due to the high power consumption of ultrasonic nebulizers, the equipment tends to be bulky. This can cause considerable difficulties, given the crowded environment that may surround a subject, such as a critical care patient.

U.S. Pat. No. 5,443,059, shows an attempt to solve the problem of bulkiness in an ultrasonic nebulizer. In the '059 patent, a liquid source and metering component are provided in separate control units that can be located at a distance from the subject. The control unit meters liquid through a feed line to a piezoelectric ceramic plate positioned in the patient limb of the breathing circuit. The piezoelectric ceramic plate nebulizes the liquid. In the event more liquid is delivered than can be nebulized, the device is equipped with a collection vessel for the excess liquid. In the structure disclosed in this patent, the metering line for the liquid to be nebulized is located above the vibrating crystal so that the liquid drops onto the crystal. However, this renders the ultrasonic nebulizer of this patent position sensitive. Additionally, during inhalation, the flow speed of the respiratory gases can exceed 10 m/s. Such a flow speed can draw the droplets of liquid away into the respiratory gases without the droplets being applied to the vibrating crystal for nebulization. This may render the inhalation therapy less effective, or may alter dosage rates, both of which can adversely affect the subject.

U.S. Pat. No. 3,812,854 describes a nebulizer for inhalation therapy in which the spray is generated on the front surface of a vibrating, porous body. The pores of the body form a network of passages that enable the liquid to flow through the body. The liquid to be nebulized is supplied under pressure from a liquid supply through a liquid conduit to the pores, and forced through the pores to the front surface of the porous body where it is discharged as a spray.

However, the complicated flow paths in the porous body increase the flow resistance so that high liquid pressure is required to transport the liquid through the body. To resist the forces resulting from the high liquid pressure, a thick porous body is required. But, such thickness increases the weight of the nebulizer as well as the amount of electric power required to vibrate it. Also, when used with suspensions containing suspended particulate or colloidal particles, the particles may be entrapped in the complicated flow paths through the porous body.

U.S. Pat. No. 5,487,378 describes a nebulizer in which the aerosol is formed using a mesh plate instead of a porous solid body, thereby to lessen or eliminate the foregoing shortcomings. The mesh plate has a plurality of orifices for the liquid in a reservoir. The orifices are tapered outwardly toward the outlet for the liquid. The liquid or the nozzle assembly is vibrated ultrasonically by a piezoelectric element to nebulize the liquid. The liquid reservoir is preferably permanently filled with liquid and maintained at a slight negative pressure.

A specific difficulty with nebulizers based on technology where the liquid or the nozzle assembly is vibrated ultrasonically by a piezoelectric element to nebulize the liquid is the nonlinear mechanical functioning of the piezoelectric element against the electrical signal frequency driving it. The mechanical movement of the piezoelectric element may be tens or hundreds times higher at a mechanical resonance frequency compared to movement outside the mechanical resonance frequency. Because of this dramatic increase in the mechanical movement at the mechanical resonance frequency, it is much more efficient to produce the vibrations to nebulize liquid at the mechanical frequency.

U.S. Pat. No. 5, 518,179 describes a nebulizer in which the aerosol is formed using a mesh plate vibrated by a piezoelectric element that has a thin-walled structure and is arranged to operate in a bending mode. The piezoelectric element has two separate, independent electrodes: a drive electrode and a sense electrode. In operation, the drive electrode is driven by an electrical signal source at an actuator mechanical resonance. While operating at this mechanical resonance, the signal from the sense electrode has a local maximum and the drive circuitry ensures that the piezoelectric element is driven close to the mechanical resonance with a phase angle between the drive and sense electrodes.

BRIEF SUMMARY OF THE INVENTION

An object of the present invention is to provide an improved nebulizer apparatus of the mesh plate type that efficiently transforms the liquid into an aerosol, but this invention can also be extended to other type of nebulizers which are run by vibrating means including a piezoelectric actuator. Another object of the invention is to provide such an apparatus that it can be easily adjusted to function at the most efficient operating point to nebulize liquid.

Furthermore, another object of the invention is to provide such an apparatus such that the state of operation for the nebulizer can be easily clarified by examining the operating point at which the vibration is produced most efficiently. By examining the state of operation, fracture of the vibrating component can be predicted and verified. By examining the state of operation, it is also possible to examine and to examine and distinguish all the broken vibrating components within the manufactured lot.

The above objects are attained by a nebulizer having vibrating means comprising a piezoelectric actuator having one or more electrode on it's surfaces or a piezoelectric vibrator having one or more electrodes on it's surfaces connected to a mechanical construction. The nebulizer further includes a frequency power service for exiting vibrator, a connecting means for connecting frequency power service to electrodes of the vibrator, and means for detecting the intensity of vibration produced by vibrating means.

Various other features, objects, and advantages of the invention will be made apparent from the following detailed description and the drawings.

BRIEF DESCRIPTION OF THE SEVERAL VIEWS OF THE DRAWING

The foregoing objects and advantages, as well as the invention itself, will be more fully understood from the attached drawing and following detailed description.

In the drawings.

DETAILED DESCRIPTION OF THE INVENTION

Figure 1:
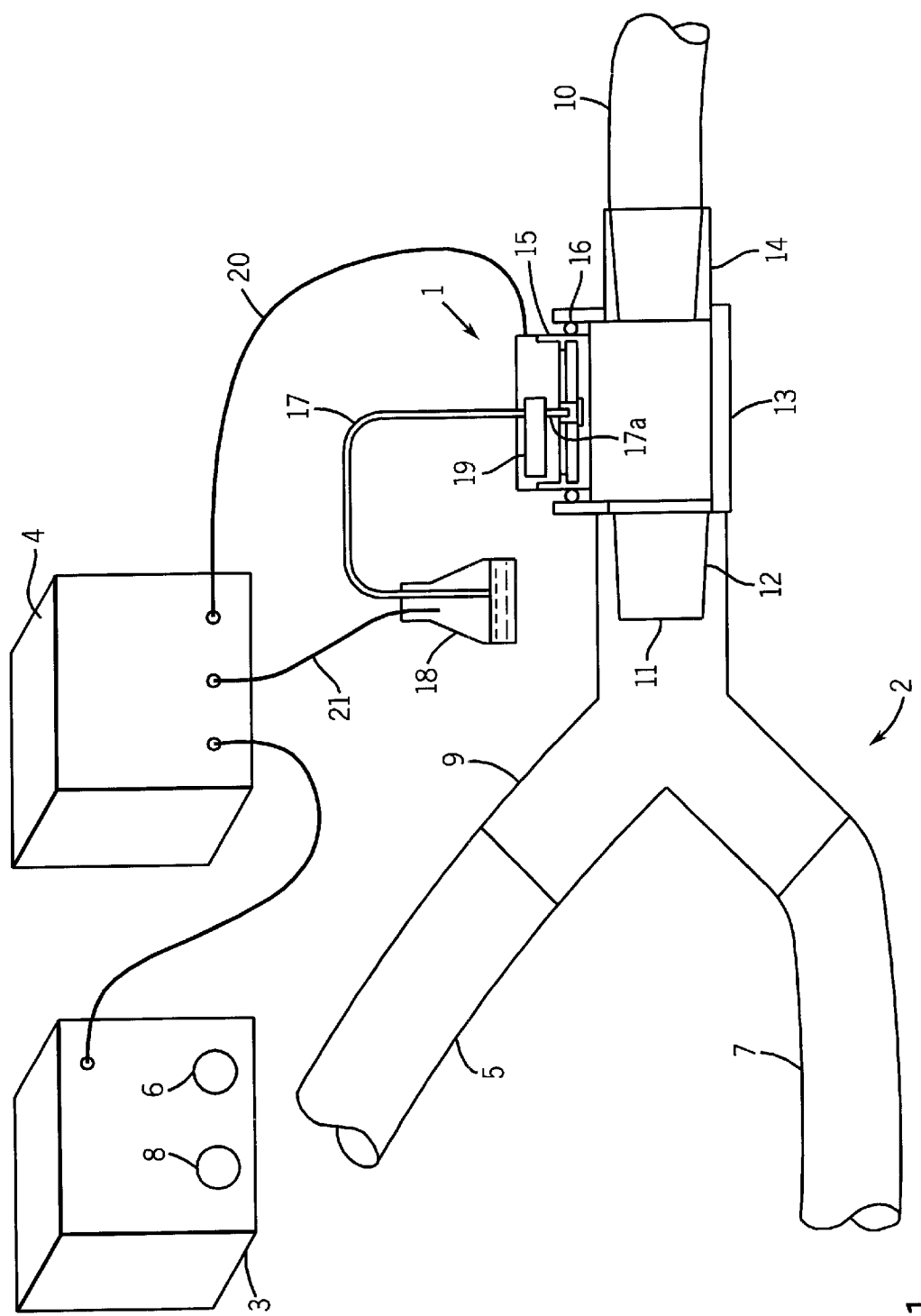
FIG. 1 is a general cross section view of the nebulizer apparatus of the present invention, the operation environment for the nebulizer apparatus being shown in a generalized schematic form.

A nebulizer apparatus 1 of the present invention is typically used in conjunction with breathing circuit 2, ventilator 3 and control unit 4, as shown in FIG. 1. The nebulizer 1 atomizes liquid solutions or suspensions for delivery to a subject, as for example as a drug treatment for a patient. Breathing circuit 2 includes inhalation limb 5, which is coupled to ventilator 3 at exhalation limb connector 6. Exhalation limb 7 is connected to ventilator 3 at inhalation limb connector 8. Inhalation limb 5 and exhalation limb 7 are connected to two arms of Y-connector 9. A third arm of Y-connector 9 is connected to one end of patient limb 10. The other end of patient limb 10 is directed to a mouthpiece, facemask, or endotracheal tube for the subject.

Ventilator 3 provides all or a portion of the respiratory gases for the subject by providing inhalation gases in inhalation limb 5. The inhalation gases pass through Y-connector 9 and into patient limb 10 for supply to the subject. On exhalation, the respiratory gases pass through patient limb 10, Y-connector 9, and exhalation limb 7 back to ventilator 3.

As shown in FIG. 1, the nebulizer apparatus 1 is preferably positioned in patient breathing circuit 2 as near the patient as possible to minimize the aerosol transport path, and to minimize the deposition of the aerosol on the breathing circuit walls. To this end, nebulizer apparatus 1 may be inserted in the breathing circuit between Y-connector 9 and patient limb 10. The Y-connector 9 has a socket 11 for receiving tubular projection 12 of adapter 13 for nebulizer apparatus 1. The tubular socket 14 of the adapter 13 receives the patient limb 10. The nebulizer apparatus is placed in opening 15 in adapter 13 and held in place with O-ring seal 16. When nebulizer apparatus 1 is not needed, or when the nebulizer apparatus is removed for cleaning or maintenance, a cap (not shown) may be fitted into or over the opening 15 to allow breathing circuit 2 to function in a normal manner. Alternatively, the entire adapter 13 containing nebulizer apparatus 1 may be removed from the breathing circuit and patient limb 10 reconnected to Y-connector 9. Control unit 4 may be located at a distance from nebulizer apparatus 1 and may be incorporated in ventilator 3, if desired.

Nebulizer apparatus 1 is connected to a source of material to be nebulized. In the embodiment shown in FIG. 1, conduit 17 and transport line 17a supply material from reservoir 18 to apparatus 1. Reservoir 18 can be placed at a desired location and can be proximate to, or remote from, nebulizer apparatus 1. A control valve 19 is provided between the supply conduit 17 and the transport line 17a. Electrical control signals are supplied to control valve 19 via cable 20 from control unit 4. As noted above, the source of material to be nebulized can comprise an aqueous solution, or a particulate or colloidal suspension, of a pharmaceutical agent. For purposes of explanation, the material undergoing nebulization is hereinafter generally described as a liquid. Reservoir 18 is pressurized by pump in control unit 4. In the embodiment shown in FIG. 1, the pump inside control unit 4 supplies a pressurizing gas to reservoir 18 through pressure line 21.

Figure 2A:
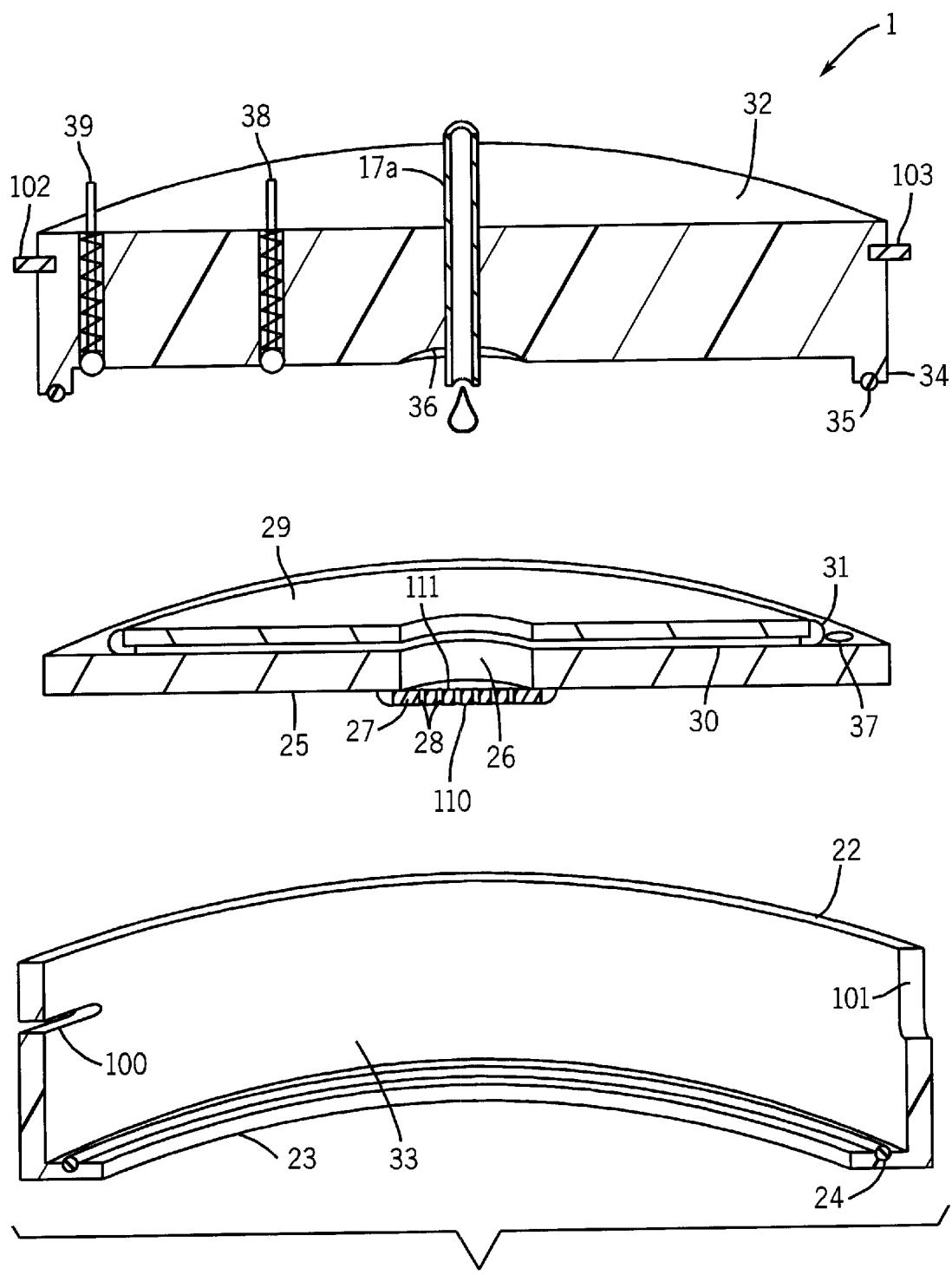
FIG. 2a is an exploded, partial view showing the nebulizer apparatus of the present invention.
Figure 2B:
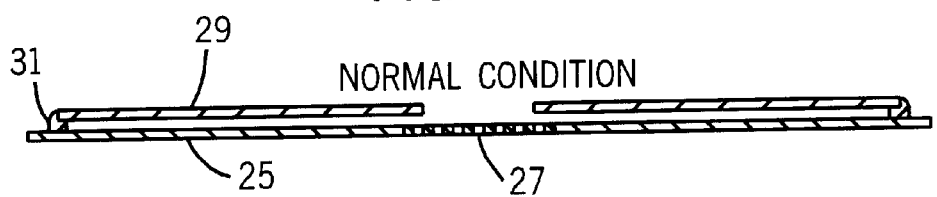
FIGS. 2b and 2c are schematic views showing the operation of the nebulizer apparatus of FIG. 1.
Figure 2C:
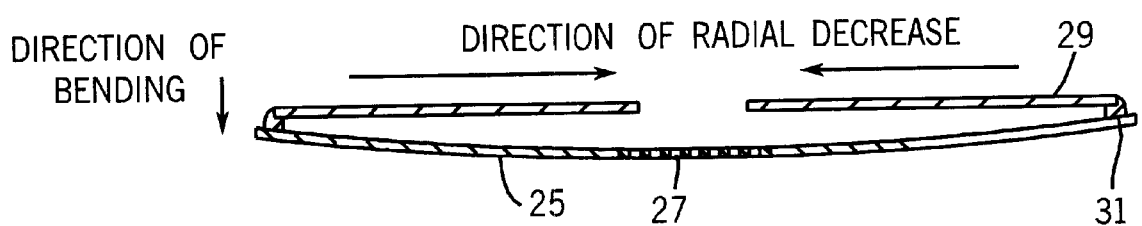

Nebulizer apparatus 1 is shown in detail in FIGS. 2a, 2b, 2c. Nebulizer apparatus 1 shown in the cross sectional, exploded view of FIG. 2a has annular housing 22, which mounts the apparatus in adapter 13. Housing 22 is formed of plastic or similar material. Lip 23 is formed on the lower edge of housing 22 and contains O-ring 24. Housing 22 is attached to plug member 32 by spiral fasting formed by opening 100 and 101. Associated ledges 102 and 103 are situated symmetrically to the sides of plug member 32 and fit into openings 100 and 101 formed in the housing 22. The housing 22 may be opened or closed by turning and pulling or turning and pushing the housing in regard to plug member 32. This allows the portions of apparatus 1 carrying out the nebulizing of the liquid, positioned in cavity 33, to be removed at the end of therapy for replacement, or for cleaning, when a different drug is to be administered to the subject.

O-ring 24 seals the disc-like plate 25, shown with enlarged thickness in FIG. 2a and comprised of a conductive material such as brass, to the lip 23. Plate 25 contains a central opening 26. A mesh plate 27, including hole 28, is attached to the lower surface of plate 25 when the nebulizer apparatus is orientated as shown in FIG. 2a. Mesh plate 27 may be mounted to plate 25 by gluing with conducting glue, brazing, welding, or other suitable technique.

Mesh plate 27 is relatively thin plate having a plurality of holes 28. Mesh plate 27 may be about 0.02 mm thick. The diameter of the holes at front surface 110 is preferably approximately 2–15 μm in diameter. Such holes may be formed in the plate by an electroforming process, which process produces holes of increasing diameter toward rear surface 111 shown in the drawing. However, straight holes will work equally well, the primary criterion being that the exit diameter in front surface 110 is such as to form droplets of the desired size.

Front surface 110 of mesh plate 27 is exposed to the pressure of the breathing gases in breathing circuit 2. These pressures will vary during inhalation and exhalation conditions in breathing circuit 2. For example, with artificial ventilation, breathing circuit pressures may increase up to 100 mbar during inspiration and thereafter decrease during expiration. Disc-like plate 25 is provided with pressure balancing channel 37, as shown in FIG. 2a, that connects volume 36 with breathing circuit 2 for equalizing the prevailing pressure at both sides of mesh plate 27. The pressure balancing provided by channel 37 prevents breathing gas from flowing through the holes in mesh plate 27, in opposition to the liquid being nebulized, which might otherwise degrade the operation of nebulizer apparatus 1 and to avoid pressure stressing of mesh plate 27 and causing leaks to occur through the mesh plate.

A vibrating element, such as a piezoelectric element 29, is mounted on the upper surface of plate 25. Specifically, the piezoelectric element 29 is spaced from plate 25 by a small gap 30 and secured to plate 25 about its periphery by a conductive glue, brazing, welding, or other suitable technique, shown as 31 in FIG. 2a. Piezoelectric element 29 has a central opening corresponding to the central opening 26 of plate 25.

Plug member 32 is formed from a non-conductive material, such as plastic, and is placed in the cavity 33 defined by the housing 22. Plug member 32 has a lower lip 34 containing an O-ring 35. Plug member 32 is placed on top of plate 25 so that the plate is between O-rings 24 and 35.

An electric power terminal 38 extends through plug member 32. The lower end of terminal 38, which terminal may be in the form of a spring-loaded pin, contacts piezoelectric element 29. The upper end of terminal 38 is connected to cable 20, as shown in FIG. 1. A second electrical power terminal 39 also extends through plug member 32. The lower end of terminal 39 contacts conductive plate 25. The upper end of terminal 39 is connected to cable 20, as shown in FIG. 1. Terminal 39 may be electrically grounded for purposes of applying a voltage to piezoelectric element 29 in conjunction with terminal 38, as well as for impedance measurement in conjunction with conductive liquid transport line 17a.

A central liquid transport line 17a extends through plug member 32 to approximately the upper surface of plate 25. A small domed cavity 36 may be formed in the lower surface of plug member 32 to surround transport line 17a. Transport line 17a may be formed of a conductive material to allow its use in impedance measurement of the presence of liquid in nebulizer apparatus 1.

In operation, valve 19 is opened in response to a signal from cable 20 and liquid flows through conduit 17 and transport line 17*a* due to the pressurizing gas in reservoir 18. The liquid flows out the end of transport line 17*a* into contact with the upper surface of mesh plate 27. The cohesive forces in the liquid create a column of liquid extending between the lower end of transport line 17*a* and mesh plate 27.

To control the transport liquid from reservoir 18 into the nebulizing apparatus 1, mesh plate 27 and transport line 17*a* function as sensing electrodes that detect the presence of liquid between the end of transport line 17*a* and the rear surface 111 of mesh plate 27 by alteration of the impedance between two "electrodes". That is, with the continued supply of liquid, the column between the end of transport line 17*a* and the rear surface 11 of mesh plate 27 will significantly alter the impedance, which is measured. A signal from the two sensing electrodes is inputted to an impedance sensor inside the control unit 4 via cable 20 and is used by the control unit 4 to control the valve 19 in the liquid supply conduit 17 to close the valve. When the impedance between the electrodes changes due to the liquid receding away from the end of transport line 17*a* and the rear surface 111 of mesh plate 27, the control valve 19 opens again to allow flow of liquid from the end of transport line 17*a*. The delivery of nebulized liquid can be controlled by continuously vibrating mesh plate 27 and regulating the liquid transport control or by regulating the activation of mesh plate vibration and intermittently supplying liquid when then amount of liquid between the mesh plate 27 and the transport line 17*a* is reduced.

In operation, alternating voltage is supplied from power source inside the control unit 4 though cable 20 and terminals 38 and 39 to the vibrating element, such as piezoelectric element 29, which vibrates the element. The alternating voltage causes the element 29 to contract from the normal condition, shown in FIG. 2*b*, to a radially decreased condition shown in FIG. 2*c* and return to the normal condition. Due to the jointer of piezoelectric element 29 to plate 25 about the periphery of the element, the radial size reduction of piezoelectric element 29 causes plate 25 to bow, as shown in FIG. 2c, and then return to the flat condition, shown in FIG. 2b, when piezoelectric element 29 returns to the normal state. The action of plate 25, as shown in FIGS. 2b and 2c, discharges nebulized liquid from holes 28 in mesh plate 27, which is also schematically shown in FIGS. 2b and 2c. At the front surface 110 of the vibrating mesh plate 27, the atomized liquid will grow into drops at each hole 28 due to the liquid surface tension. The drops will increase in size until the expelling forces arising from the movement of mesh plate 27 and the mass of each drop exceeds the holding force determined by the size of the holes 28 in mesh plate 27 and the surface tension of the liquid. The drops expelled from plate 27 pass through the housing 22 into the patient limb 10, and to the subject during inhalation.

Figure 3A:
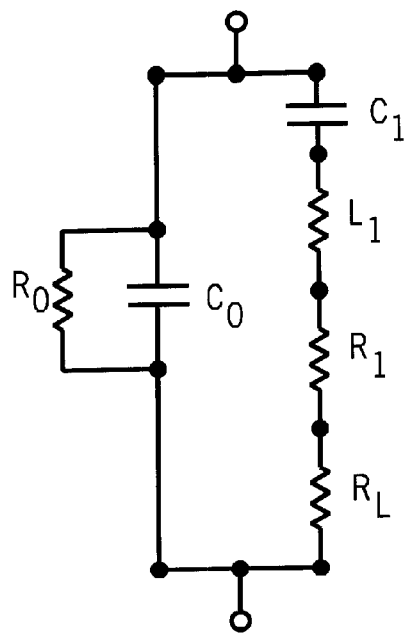
FIGS. 3a and 3b are schematic views representing electrical properties of a piezo crystal.

When an alternating voltage is applied to the electrodes of the piezoelectric element 29, the dynamic behavior of the element will be quite different at the frequency of mechanical resonance compared to the piezoelectric element's behavior at static state. The maximum amplitude of mechanical displacement induced by an alternating field may be much greater than the maximum static displacement. A piezoelectric transducer, operating near or at the mechanical resonant frequency can be characterized by simple equivalent circuit shown in FIG. 3a. In the equivalent circuit, $C_0$ is the capacitance of the clamped transducer and $R_0$ is dielectric loss of the transducer. $R_1$ represents the mechanical loss in the transducer and $R_L$ represents the acoustic or mechanical load. $C_1$ and $L_1$ represent the rigidity and the mass of the material.

Figure 3B:
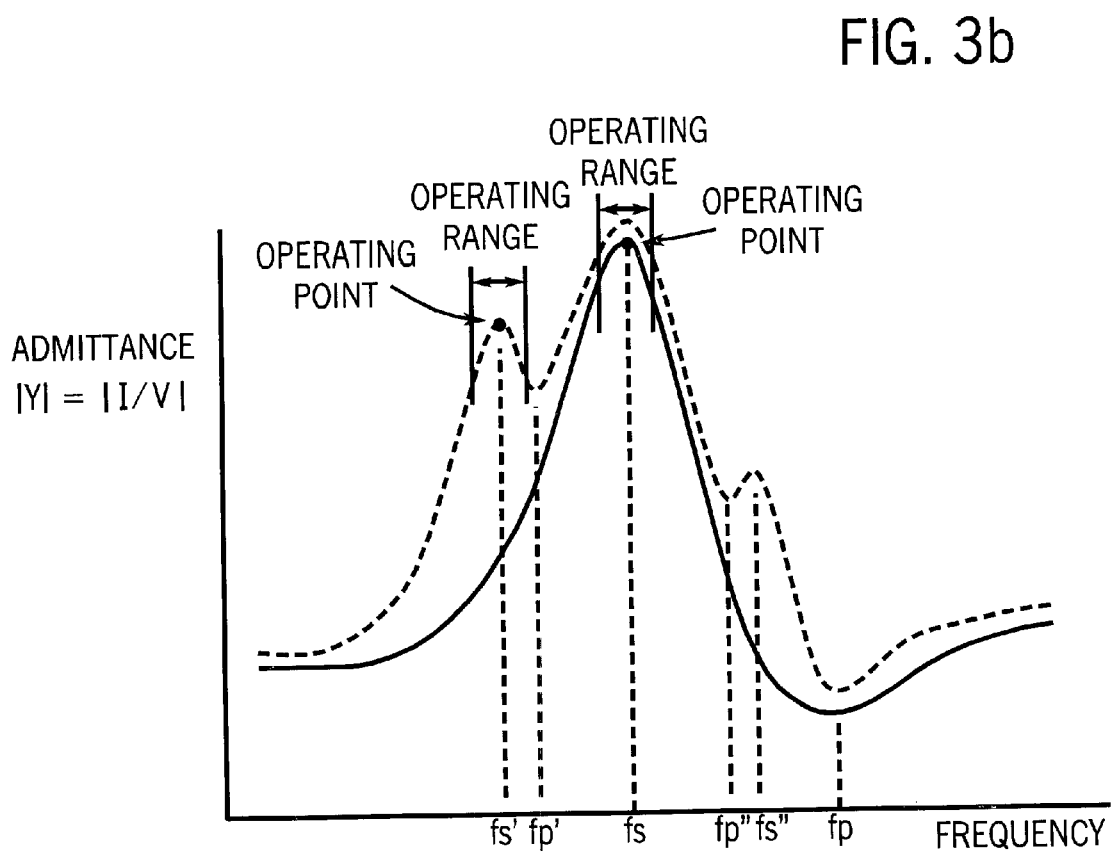

If the electrical admittance Y of the vibrating transducer is plotted against the frequency, one obtains the following resonant curve shown in FIG. 3b, plotted as a uniform line. The frequency $f_s$, at which the admittance is maximum, is called the series resonant frequency. The minimum value of the admittance is found at frequency $f_p$, which is called the parallel resonant frequency.

The frequency of mechanical resonance can be fixed by changing the external measurements of the piezoelectric element or by changing the composition of piezoelectric material.

When the piezoelectric element is attached to other mechanical construction as shown in FIG. 2, the construction affects to the mechanical resonant frequency of the piezoelectric element. Attached construction functions as a mechanical load to piezoelectric transducer and this can be observed as a change in series resonant frequency $f_s$ and as a change in parallel resonant frequency $f_p$. The absolute maximum amplitude of mechanical displacement induced by an alternating electric field is achieved at series resonant frequency point $f_s$, at which the admittance is maximum and this point can be called the optimum operating point.

Additionally, apportioning of liquid on to the vibrating mesh plate 27 also affects the piezoelectric transducer as a mechanical load and thus changes the series resonant frequency point $f_s$. The series resonant frequency point shifts from the operating point, the original series resonant frequency point, when a liquid drop arrives on the vibrating mesh plate. After the liquid drop has broken in to an aerosol, the series resonant frequency point shifts back to the operating point, the original series resonant frequency point. This change in series resonant frequency caused by the apportioned liquid on to a vibrating mesh plate, defines the operating range for the frequency around the chosen operating point as shown in FIG. 3b.

Figure 4:
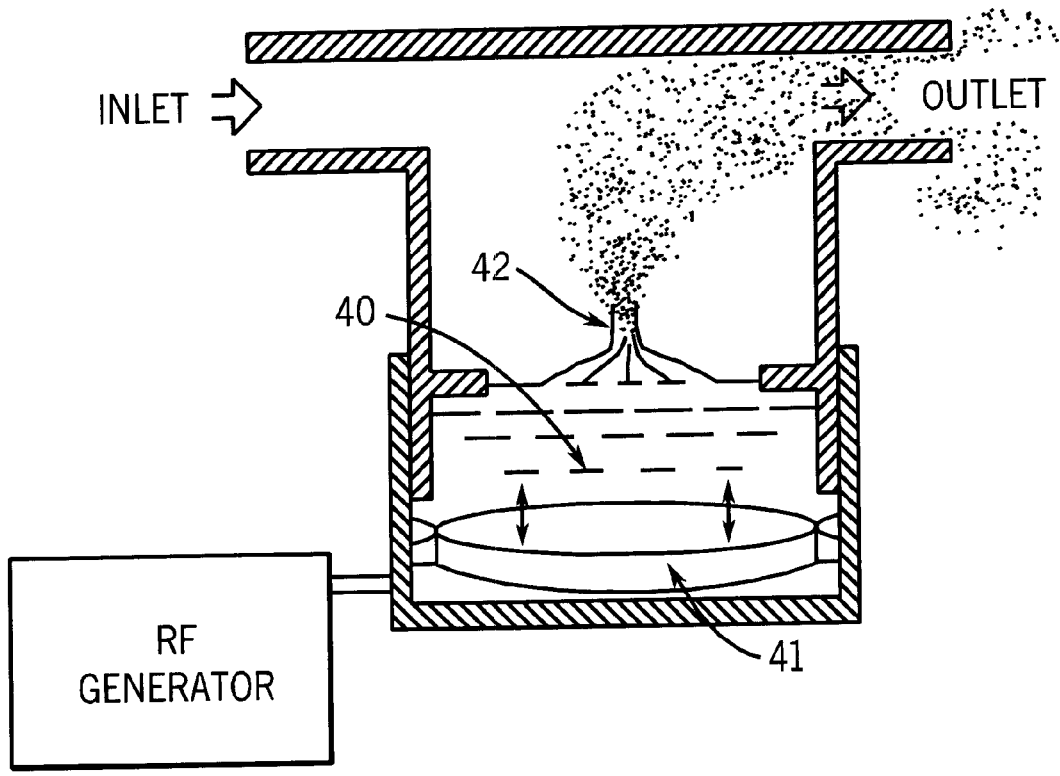
FIG. 4 is a schematic view of an ultrasonic nebulizer.

Another example of a nebulizer based on the piezoelectric vibrator, where the construction and apportioned liquid has an effect on the series resonant frequency point and the efficiency of the piezoelectric element, is an ultrasonic nebulizer which principle of operation is shown in FIG. 4. In ultrasonic nebulizers, the fine spray is produced by ultrasonic vibration of the liquid 40, as by a piezoelectric crystal 41. The liquid 40 is dropped on, or otherwise applied to, the crystal 41. In the case when liquid is dropped on to the piezoelectric element, the vibration of piezoelectric element breaks the apportioned fluid in to an aerosol straight from the surface of the piezoelectric element. When piezoelectric element is totally embedded with liquid, vibrations of the piezoelectric element are transferred and brought into focus on the surface of liquid. A source 42 is being formed into the focus on the surface of the liquid where the aerosol comes off.

The mechanical construction attached to piezoelectric element or some parts of the attached mechanical construction do not necessarily vibrate at the same frequencies as the piezoelectric element. These vibrations can be seen as lower or higher order modes of vibration and so there will be one or more series resonant frequencies $f_s'$, at which the admittance has local maximums and parallel resonant frequencies $f_p'$, at which the admittance has local minimums. In FIG. 3b, where the electrical admittance Y of the vibrating transducer as plotted against the frequency, there is shown an electrical admittance Y of the vibrating transducer is plotted against the frequency as well as a dashed line illustrating the electrical admittance for the piezoelectric element when it is attached to a mechanical construction forming lower or higher order modes of vibration. Frequency points $f_s'$ and $f_s''$ are modes of lower and higher order series resonant frequencies and points $f_p'$ and $f_p''$ are made of lower and higher order parallel resonant frequencies. These lower or higher order series resonant points can also be used to operate the vibrating element at local maximum displacement levels to produce aerosol if the absolute maximum of series resonant frequency point is out of the desired frequency range.

In order that the vibrating transducer functions at the series resonant frequency point, so that the mechanical displacement induced by an alternating electric field is enough to produce aerosol efficiently, the amplitude of voltage supplied to the piezoelectric element must be high enough. If it is desired to expand the frequency range where the operating point can vary to produce aerosol, the amplitude of voltage supplied to piezoelectric element can be increased. If the absolute maximum of series resonant frequency point is out of the desired frequency range, the lower or higher order series resonant frequency points can also be used to operate the vibrating element at local maximum displacement levels to produce aerosol by increasing the amplitude of voltage supplied to piezoelectric element.

In general, the frequency range for operating point, where the mechanical displacement induced by an alternating electric field is enough to produce aerosol the most efficiently, is achieved when the amplitude of the admittance has not decreased lower than −1 dB from the absolute or local optimum operating point. Inversely, at that state the amplitude of voltage supplied to piezoelectric element must be higher than the minimum voltage needed to produce aerosol at the absolute or local maximum displacement level.

A useful frequency range for the operating point is achieved for amplitudes of admittance down to −3 dB from absolute or local optimum operating point, but inversely the amplitude of voltage supplied to piezoelectric element must then be much higher than the minimum voltage needed to produce aerosol at the absolute or local maximum displacement level, so better results will be achieved for amplitudes of admittance higher than −2 dB.

Figure 5A:
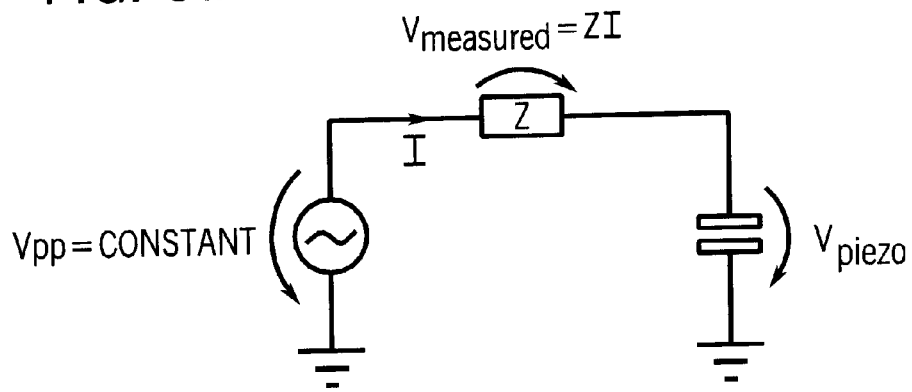
FIGS. 5a, 5b, and 5c are schematic views representing electrical couplings for measuring the electrical properties of a piezo crystal.

In applications accomplished by using the piezoelectric element to produce maximum mechanical movement of the piezoelectric element into one or more directions at some frequency, the frequency point where the maximum mechanical movement is attained or the frequency range for some level of mechanical movement near the maximum can be found by measuring the current taken by the piezoelectric element against the signal frequency. An example of a circuit for measuring the current taken by the piezoelectric element against the signal frequency is shown in a FIG. 5a. When the amplitude of voltage of the alternating electric signal applied to piezoelectric element is maintained constant, the current consumption of the piezoelectric element is highest at the point of series resonant frequency $f_s$ and correspondingly lowest at the point of parallel resonant frequency $f_p$.

Figure 5B:
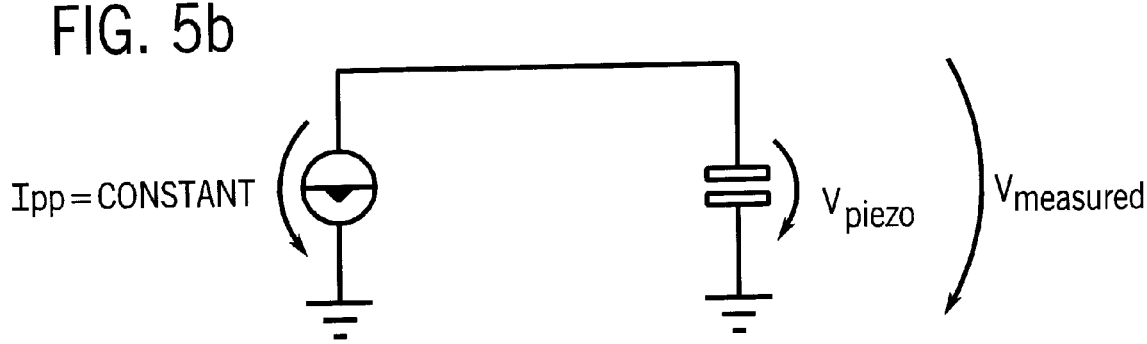

Alternatively, when the electric current of the alternating electric signal applied to piezoelectric element is maintained constant, the change in voltage caused by the impedance change of the piezoelectric element can be measured against the signal frequency. Measured voltage is the lowest at the point of series resonant frequency $f_s$ and correspondingly highest at the point of parallel resonant frequency $f_p$. An example of a circuit measuring the change in voltage caused by the impedance change of the piezoelectric element against the signal frequency is shown in a FIG. 5b.

Figure 5C:

Another technique is to measure the difference in phase angle between the alternating electric signal applied to piezoelectric element and the signal in the node after the piezoelectric element. The point of series resonant frequency $f_s$, where the mechanical movement is maximum, is at a point where the difference between phase angles of the alternating electric signal applied to piezoelectric element and the signal in the node after the piezoelectric element is zero. An example of a circuit measuring the difference in phase angle against the signal frequency between the alternating electric signal applied to piezoelectric element and the signal in the node after the piezoelectric element is shown in a FIG. 5c.

Figure 6A:
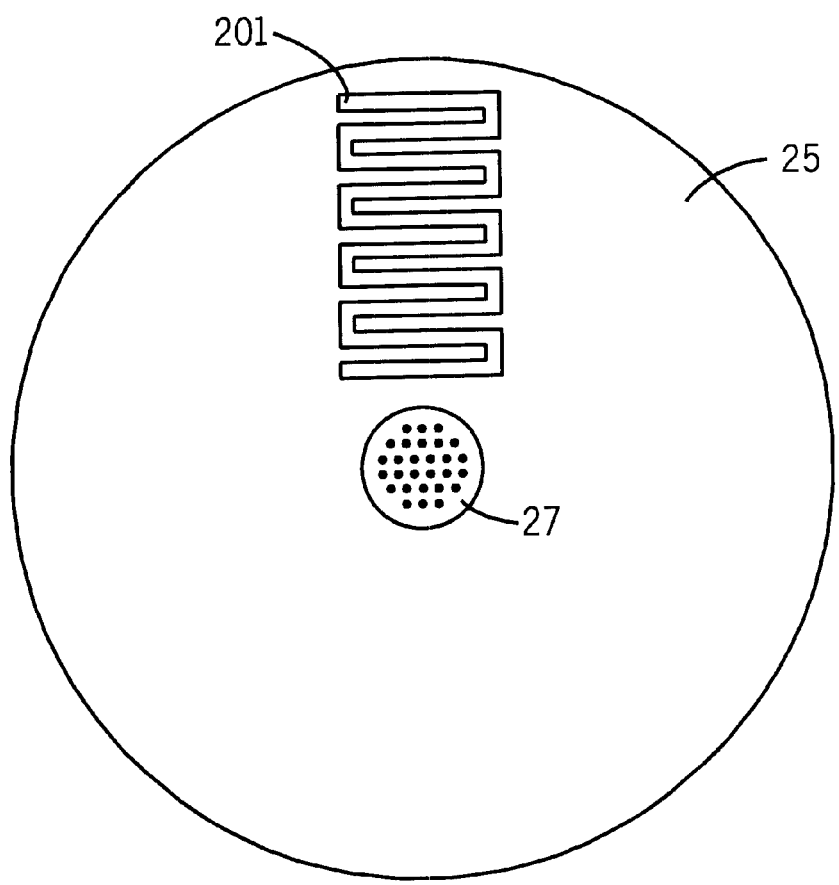
FIGS. 6a and 6b are schematic views representing the piezoelectric vibrator and an electrical coupling according the present invention.
Figure 6B:
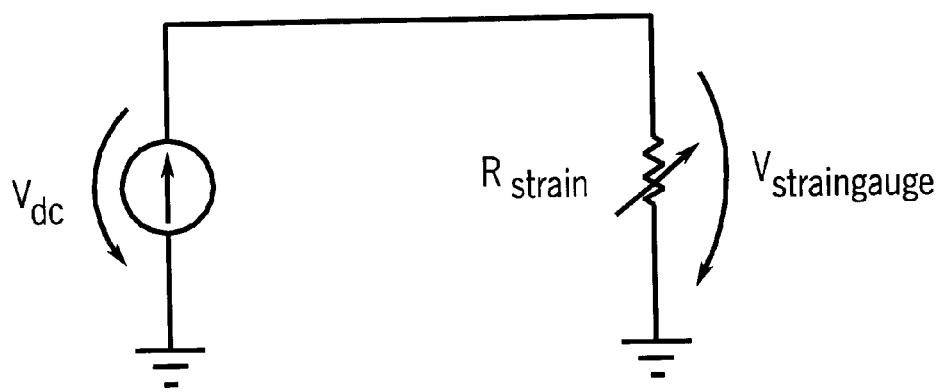

A different technique is to measure the magnitude of movement in vibrating structure by strain gauge attached to structure. FIG. 6a shows an example of such a structure, which is a plan view of the bottom side of structure formed by disc-like plate 25, mesh plate 27 and piezoelectric element 29 shown in a FIG. 2a. Vibrating motion of the disc-like plate 25 stretches the strain gauge 201, which causes variations in resistance of the strain gauge 201. These variations in resistance can be measured with electronic circuit to find a point for series resonance frequency $f_s$. An example of a circuit measuring the strain caused by vibrations of the piezoelectric element against the signal frequency is shown in a FIG. 6b. However, the disadvantage of this principle is the limited measuring range in frequency from zero only to a few tens of kHz.

There are many advantages achieved by measuring the current, voltage or phase angle taken by the piezoelectric element when the element is vibrated or using a strain gauge attached to structure to measure the resistance when the element is vibrated.

Figure 7A:
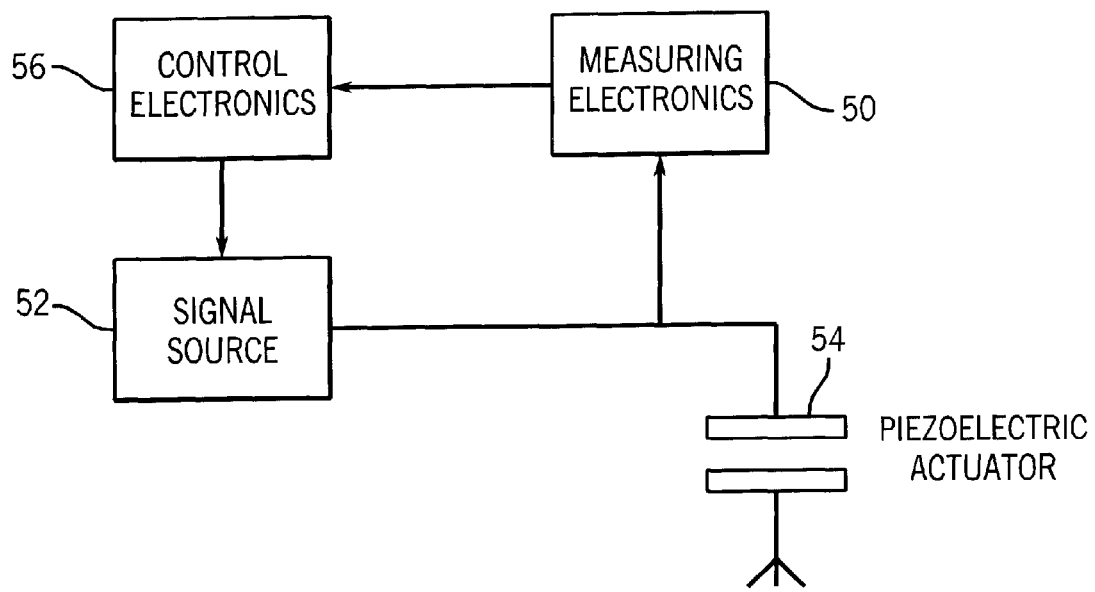
FIGS. 7a and 7b are schematic views representing examples of two different control systems for the piezoelectric vibrator.
Figure 7B:
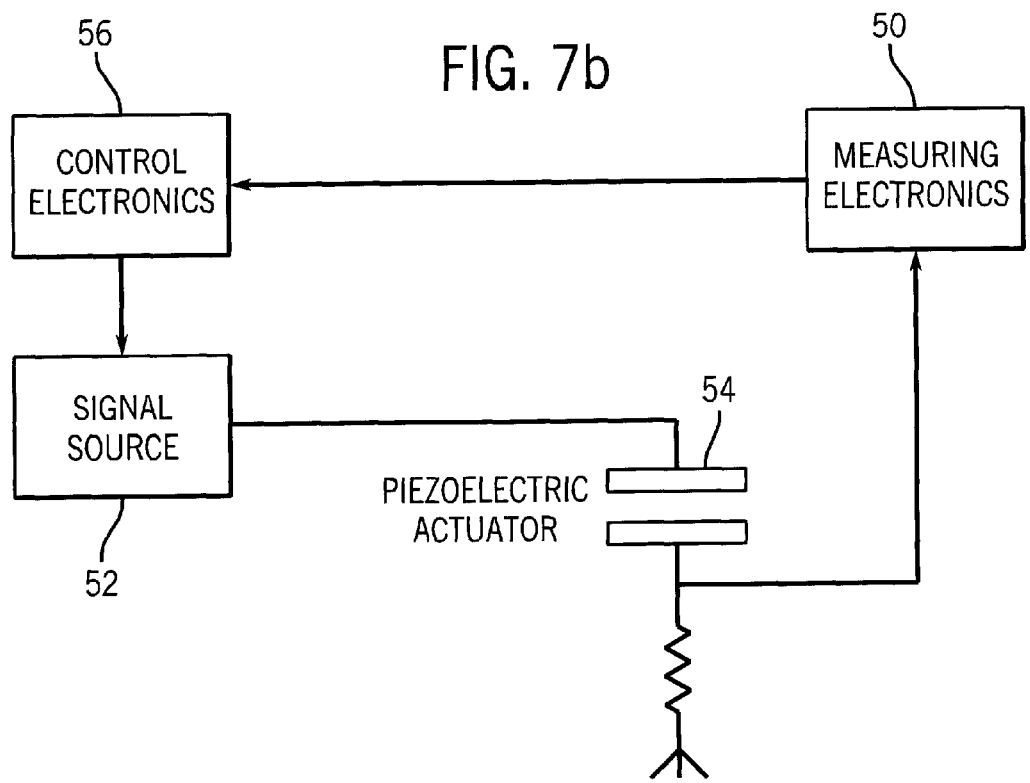

In spite of the tolerances and differences in the production line of the actuator elements, the optimum controlling frequency range, where the aerosol is produced most efficiently, can be found automatically for each actuator element. Two examples of such automated electronic circuits are shown in FIGS. 7a and 7b. In FIG. 7a, measuring electronics 50 are shown positioned to monitor the signal from the signal source 52 prior to the signal reaching the piezoelectric actuator 54. The control electronics 56 are positioned between the measuring electronics 50 and the signal source 52 to provide adaptive feedback to control the signal source 52. FIG. 7b illustrates a similar system in which the measuring electronics 50 measure operating parameters after the piezoelectric actuator 54. The measuring electronics 50 provide measured signals back to the control electronics 56, which again control operation of the signal source 52. Automated tuning makes functioning of the apparatus the most efficient and reliable and enables quick and easy changing of vibrator element, which is vitally important for a disposable product.

If the vibrating construction vibrated by the piezoelectric element is formed of one or more different elements, the maximum amplitude of vibration on the mesh plate to produce the aerosol efficiently may also be found at lower or higher order modes of vibration. These local series resonant frequencies, for example $f_s'$, are found by measuring techniques described earlier and can be used alternatively if the frequency point of absolute maximum is too high or too low in frequency.

Figure 8:
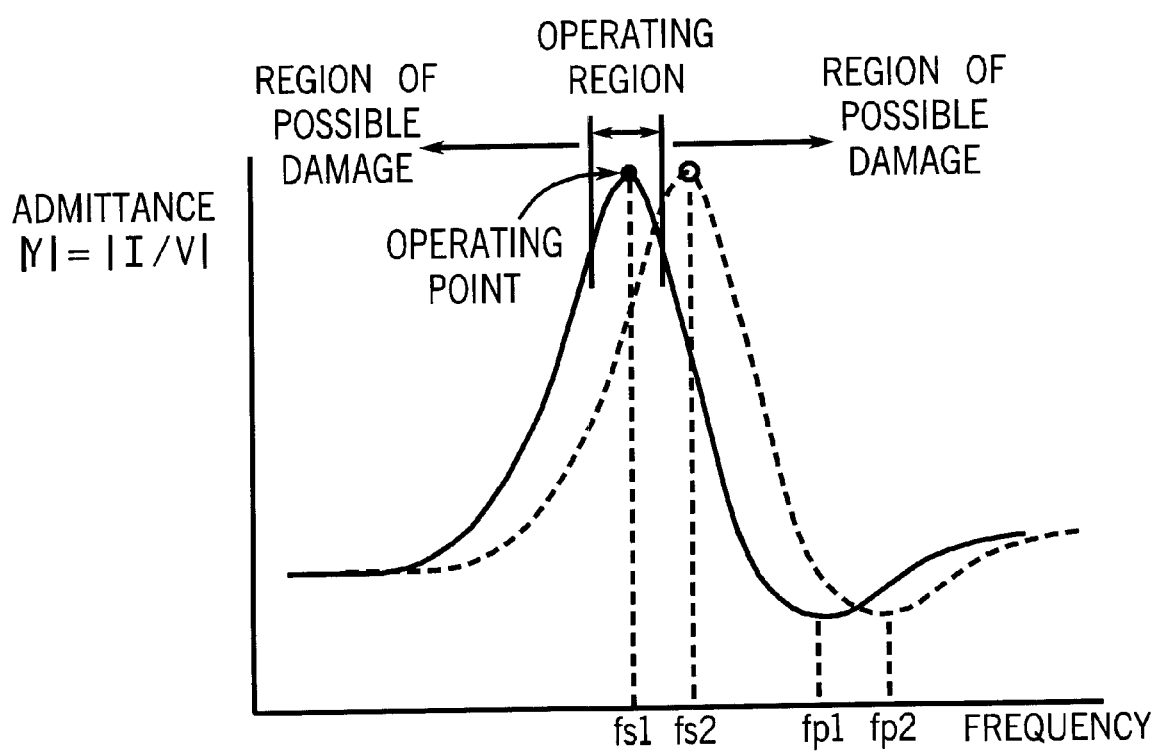
FIG. 8 is a graphic depiction of the shift in the frequency axis when the vibrating element of the nebulizer has been damaged.

The state of operation can be easily clarified by examining changes in the operating point, where the vibration is produced most efficiently to produce aerosol. By examining the state of operation against frequency or phase, breaking of the vibrating component can be predicted and verified. If, for example, the fastening between disc-like plate 25 and the piezoelectric element 29 in FIG. 2 or if mesh plate 27 attached to disc-like plate 25 in FIG. 2a is fractured, the unfastening or fracture causes an immediate change in the mechanical properties of the vibrator and also to the electric properties of piezoelectric element. The optimum mechanical resonant frequency is immediately shifted in the frequency axes out of the normal operating range, which is shown in FIG. 8. The uniform line in FIG. 8 represents the normal condition where the vibrating element is unbroken and has a series resonant frequency at a point $f_{s1}$. The dashed line in FIG. 8 represents a condition where the vibrating element has broken up and the series resonant frequency has been shifted to frequency point $f_{s2}$ from the point $f_{s1}$. This shift in frequency can be easily measured with the electronic circuits previously presented.

In production line examining of the optimum controlling frequency, where the aerosol is produced most efficiently and examining of the state of operation can be used for accurate, fast, and automatic detection of flawed components.

By examining the state of operation against frequency or phase, the case when the vibrating element is incorrectly placed between housing 22 and plug member 32 in FIG. 2a can also be examined. When the vibrating element is placed incorrectly, forces directed to vibrator element by housing 22 and plug member 32 causes a deviation in series resonance frequency fs, which is measured. Improper or missing of the electrical connections to the vibrating element or the case where the connections are soiled can be determined because the frequency response to the piezoelectric element is flat or low in amplitude.

Although the vibrating element is described in the specification and shown in the drawings as being the piezoelectric element 29, it is contemplated by the inventor that various other types of elements that function in the same manner could be substituted for the piezoelectric element 29. In general, the vibrating element must create a sufficient mechanical displacement to cause a liquid supply to be atomized as described previously. Additionally, the mesh plate 27 could be replaced with other types of equivalent atomizing elements that function to form droplets, such as for example the liquid cup utilized in an ultrasonic nebulizer.

It is recognized that other equivalents, alternatives, and modifications aside from those expressly stated, are possible and within the scope of the appended claims.

I claim:

1. A method for operating a nebulizer apparatus near one of several maximum mechanical displacement levels to atomize a liquid into an aerosol of fine droplets, the method comprising the steps of:
   providing an vibrating element to form the droplets;
   supplying the liquid to the vibrating element, the vibrating element being movable between a first state and a second state upon application of voltage to the vibrating element;
   connecting a voltage source to the vibrating element to cause the vibrating element to oscillate between the first state and the second state, the voltage source having an adjustable frequency;
   measuring an electric characteristic of the nebulizer apparatus, the electric characteristic having a known relationship to one of several series resonant frequencies at which the vibrating element reaches one of the maximum mechanical displacement levels; and
   adjusting the frequency at which the voltage source is supplied to the vibrating element until the measured electric characteristic is within −2 dB of the electric characteristic corresponding to one of the series resonant frequencies.

2. The method of claim 1 wherein the series resonant frequencies include an absolute maximum series resonant frequency and at least two local maximum frequencies which are modes of lower and higher order series resonant frequencies.

3. The method of claim 2 wherein the frequency of the voltage source is adjusted until the measured electric characteristic reaches a value corresponding to the absolute maximum series resonant frequency such that the vibrating element has an absolute maximum mechanical displacement.

4. The method of claim 2 wherein the frequency of the voltage source is adjusted until the measured electric characteristic reaches a value corresponding to one of local maximum frequencies which are lower and higher order series resonant frequencies when the absolute maximum series resonant frequency is out of a desired frequency range.

5. The method of claim 1 wherein the vibrating element is attached to an atomizing element to form the droplets.

6. The method of claim 5 wherein the atomizing element is a mesh plate having a plurality of holes to form the droplets.

7. A method for operating a nebulizer apparatus near one of several maximum mechanical displacement levels to atomize a liquid into an aerosol of fine droplets, the method comprising the steps of:
   providing an vibrating element to form the droplets;
   supplying the liquid to the vibrating element, the vibrating element being movable between a first state and a second state upon application of voltage to the vibrating element;
   connecting a voltage source to the vibrating element to cause the vibrating element to oscillate between the first state and the second state, the voltage source having an adjustable frequency;
   measuring an electric characteristic of the vibrating element between a pair of terminals in contact with the vibrating element of the nebulizer apparatus, the admittance having a known relationship to one of several series resonant frequencies at which the vibrating element reaches one of the maximum mechanical displacement levels; and
   adjusting the frequency at which the voltage source is supplied to the vibrating element until the measured admittance between the pair of terminals reaches a value corresponding to one of the series resonant frequencies.

8. The method of claim 7 wherein the frequency of the voltage source is adjusted until the admittance reaches a maximum value, wherein the maximum value of the admittance of the vibrating element corresponds to the series resonant frequency.

9. The method of claim 8 wherein the frequency of the voltage source is adjusted until the admittance is within −2 dB of the admittance corresponding to one of the series resonant frequencies.

10. A method for operating a nebulizer apparatus near one of several maximum mechanical displacement levels to atomize a liquid into an aerosol of fine droplets, the method comprising the steps of:
    providing an vibrating element to form the droplets;
    supplying the liquid to the vibrating element, the vibrating element being movable between a first state and a second state upon application of voltage to the vibrating element;
    connecting an alternating voltage source to the vibrating element to cause the vibrating element to oscillate between the first state and the second state, the voltage source having an adjustable frequency;
    measuring an electric characteristic of the vibrating element between a pair of terminals in contact with the vibrating element of the nebulizer apparatus, the electric characteristic having a known relationship to one of several series resonant frequencies at which the vibrating element reaches one of the maximum mechanical displacement levels; and
    adjusting the frequency at which the voltage source is supplied to the vibrating element until the measured electric characteristic reaches a value corresponding to one of the series resonant frequencies,
    wherein the alternating voltage source has a constant magnitude and the step of measuring an electric characteristic of the nebulizer apparatus includes the steps of measuring a current passing between the pair of terminals in contact with the vibrating element and adjusting the frequency of the alternating voltage source until the current passing between the pair of terminals is maximized.

11. A method for operating a nebulizer apparatus near one of several maximum mechanical displacement levels to atomize a liquid into an aerosol of fine droplets, the method comprising the steps of:
    providing an vibrating element to form the droplets;
    supplying the liquid to the vibrating element, the vibrating element being movable between a first state and a second state upon application of voltage to the vibrating element;
    connecting an alternating voltage source to the vibrating element to cause the vibrating element to oscillate between the first state and the second state, the voltage source having an adjustable frequency;

measuring an electric characteristic of the vibrating element between a pair of terminals in contact with vibrating element of the nebulizer apparatus, the electric characteristic having a known relationship to one of several series resonant frequencies at which the vibrating element reaches one of the maximum mechanical displacement levels; and adjusting the frequency at which the voltage source is supplied to the vibrating element until the measured electric characteristic reaches a value corresponding to one of the series resonant frequencies, wherein a current supplied by the alternating voltage source is constant and the step of measuring an electric characteristic of the nebulizer apparatus includes the steps of measuring a magnitude of the alternating voltage source between the pair of terminals and adjusting the frequency of the alternating voltage source until the magnitude of the alternate voltage source measured between the pair of terminals is minimized.

12. A method for operating a nebulizer apparatus near one of several maximum mechanical displacement levels to atomize a liquid into an aerosol of fine droplets, the method comprising the steps of:

providing an vibrating element to form the droplets;

supplying the liquid to the vibrating element, the vibrating element being movable between a first state and a second state upon application of voltage to the vibrating element;

connecting an alternating voltage source to the vibrating element to cause the vibrating element to oscillate between the first state and the second state, the voltage source having an adjustable frequency;

measuring an electric characteristic of the vibrating element between a pair of terminals in contact with the vibrating element of the nebulizer apparatus, the electric characteristic having a known relationship to one of several series resonant frequencies at which the vibrating element reaches one of the maximum mechanical displacement levels; and adjusting the frequency at which the voltage source is supplied to the vibrating element until the measured electric characteristic reaches a value corresponding to one of the series resonant frequencies, wherein the alternating voltage source has an operating phase and the operating phase is maintained constant and the step of measuring an electric characteristic of the nebulizer apparatus includes measuring a modified phase of a modified alternating voltage at a node after the vibrating element and adjusting the frequency of the alternating voltage source until the modified phase of the modified voltage measured at the node after the vibrating element is equal to the operating phase of the alternating voltage source.

13. A method for operating a nebulizer apparatus near one of several maximum mechanical displacement levels to atomize a liquid into an aerosol of fine droplets, the method comprising the steps of:

providing an vibrating element to form the droplets;

supplying the liquid to the vibrating element, the vibrating element being movable between a first state and a second state upon application of voltage to the vibrating element;

connecting an alternating voltage source to the vibrating element to cause the vibrating element to oscillate between the first state and the second state, the voltage source having an adjustable frequency;

measuring an electric characteristic of the vibrating element between a pair of terminals in contact with the vibrating element of the nebulizer apparatus, the electric characteristic having a known relationship to one of several series resonant frequencies at which the vibrating element reaches one of the maximum mechanical displacement levels;

adjusting the frequency at which the voltage source is supplied to the vibrating element until the measured electric characteristic reaches a value corresponding to one of the series resonant frequencies; and providing a strain gauge on a surface of the vibrating element, the strain gauge generating a signal related to a magnitude of mechanical movement of the vibrating element, and adjusting the frequency of the alternating voltage source until the signal from the strain gauge is maximized.

14. A method of operating a nebulizer apparatus at a maximum mechanical displacement level to atomize a liquid into an aerosol of fine droplets, the nebulizer including a mesh plate having a plurality of holes to form the fine droplets, the mesh plate being attached to a piezoelectric element operable to vibrate the mesh plate, the method comprising the steps of:

positioning a transport line to supply the liquid to the mesh plate for atomization;

positioning a pair of terminals in contact with the piezoelectric element;

connecting an alternating voltage source having an adjustable frequency to the pair of terminals in contact with the piezoelectric element to cause the piezoelectric element to repeatedly oscillate between a normal state and a contracted state, wherein the oscillation between the normal state and the contracted state causes the mesh plate to vibrate;

measuring an electric characteristic of the nebulizer apparatus, the electric characteristic having a known relationship to an admittance of the piezoelectric element between the pair of terminals; and calculating the admittance between the pair of terminals based upon the measured electric characteristic;

adjusting the frequency of the alternating voltage source until the admittance of the piezoelectric element between the pair of terminals reaches a maximum value, the maximum value of the admittance corresponding to a series resonant frequency for the piezoelectric element at which the piezoelectric element has a maximum mechanical displacement.

15. The method of claim 14 wherein an alternating voltage generated by the alternating voltage source has an amplitude and the measured electric characteristic of the nebulizer apparatus is a current present between the pair of terminals when the amplitude of the alternating voltage source is held constant.

16. The method of claim 14 wherein the measured electric characteristic is a voltage measured between the pair of terminals when a current generated by the alternating voltage source is held constant.

17. The method of claim 14 wherein the alternating voltage is operated having an operating phase and the measured electric characteristic is a modified phase of a modified voltage at a node after the piezoelectric element, wherein the operating phase of the alternating voltage source is constant and the frequency of the alternating voltage source is adjusted until the modified phase of the modified voltage at the node equals the operating phase of the alternating voltage source.

18. A method for operating a nebulizer apparatus at a maximum mechanical displacement level to atomize a liquid into an aerosol of fine droplets, the method comprising the steps of:

providing a mesh plate having a plurality of holes to form the droplets;

supplying the liquid to the mesh plate;

attaching a vibrating element to the mesh plate, the vibrating element being movable between a contracted state and a normal state upon application and removal of voltage;

connecting an alternating voltage source having an adjustable frequency to the vibrating element to cause the vibrating element to oscillate between the normal state and the contracted state and vibrate the mesh plate;

measuring an electric characteristic of the nebulizer apparatus, the electric characteristic having a known relationship to a series resonant frequency at which the piezoelectric element has a maximum mechanical displacement;

continuously adjusting the frequency of the alternating voltage source supplied to the vibrating element until the measured electric characteristic reaches a value corresponding to the series resonant frequency; and monitoring for changes in the value of the measured electric characteristic corresponding to the series resonant frequency during operation of the nebulizer apparatus, the changes in the value of the measured electric characteristic corresponding to the series resonant frequency indicating a failure in the nebulizer apparatus.

19. The method of claim 18 wherein the vibrating element is a piezoelectric element.

20. The method of claim 19 further comprising the steps of:

determining a base line series resonant frequency during normal operation of the nebulizer apparatus; and comparing the base line series resonant frequency to a current series resonant frequency to identify changes in the series resonant frequencies to indicate a failure in the nebulizer apparatus.

* * * * *